United States Patent [19]

Mower

[11] Patent Number: 5,111,815
[45] Date of Patent: May 12, 1992

[54] METHOD AND APPARATUS FOR CARDIOVERTER/PACER UTILIZING NEUROSENSING

[75] Inventor: Morton M. Mower, Edina, Minn.

[73] Assignee: Cardiac Pacemakers, Inc., St. Paul, Minn.

[21] Appl. No.: 597,378

[22] Filed: Oct. 15, 1990

[51] Int. Cl.5 ............................................ A61N 1/362
[52] U.S. Cl. ........................ 128/419 PG; 128/419 D
[58] Field of Search ......... 128/419 PG, 419 C, 419 D

[56] References Cited

U.S. PATENT DOCUMENTS

| | | | |
|---|---|---|---|
| 4,201,219 | 5/1980 | Gonzalez | 128/419 PG |
| 4,590,946 | 5/1986 | Loeb | 128/642 |
| 4,791,931 | 12/1988 | Slate | 128/419 PG |

Primary Examiner—William E. Kamm
Assistant Examiner—Scott M. Getzow
Attorney, Agent, or Firm—Haugen and Nikolai

[57] ABSTRACT

A method and apparatus for cardioverter/pacemaking utilizing neurosensing. The invention utilizes the baroreceptor nerves found in the body. A neurosense electrode is placed around the carotid sinus nerve and a sense amplifier with automatic gain control and an integral band pass filter provides a frequency-to-voltage converter with a frequency proportional to the stimulus received from the carotid sinus nerve. The voltage from the frequency-to-voltage converter is sent to the analog-to-digital converter where it is bussed to a microprocessor. The microprocessor then drives a pacing lead and in the presence of a cardiac signal the microprocessor provides a cardioverting signal to the cardioverting lead if ventricular arrhythmia is sensed. The microprocessor also drives a telemetry coil and receives ventricular information from the ventricular sensing lead.

23 Claims, 3 Drawing Sheets

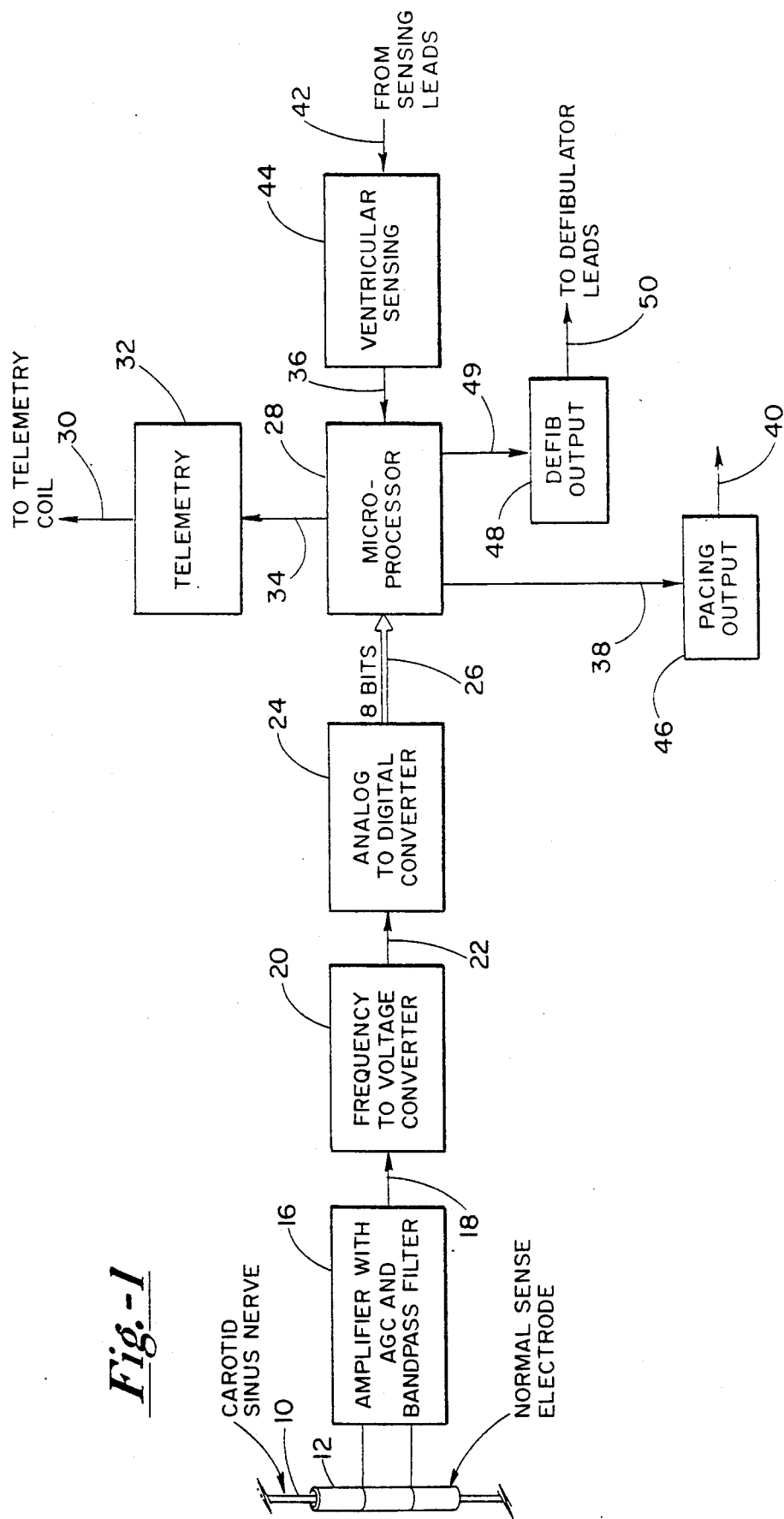

METHOD AND APPARATUS FOR CARDIOVERTER/PACER UTILIZING NEUROSENSING

BACKGROUND OF THE INVENTION

The present invention relates to an automatic cardiodefibrillating pacemaker having electrical pulses controlled by regulation signals detected in the nerves. The background of neurosensing for cardiac pacemaking is generally discussed in José L. Bozal Gonzales of Spain U.S. Pat. No. 4,201,209. Gonzales discloses a method of pacing the heart utilizing a signal from the carotid sinus glomus which is the main feedback mechanism of the body to control the sinus node. Gonzales attempts to provide the capacity to regulate pacemaker rhythm in response to the biological needs of the patient during activity. A normal heart controls the rhythm of its beat to regulate the supply of blood to the various tissues in the body. Therefore, a person needs a higher blood flow when engaged in strenuous activity than when at rest. Although Gonzales discloses a method of pacemaking using the carotid sinus nerve he does not provide, a method of cardioverting or pacemaking coupled with cardioverting or defibrillating.

In U.S. Pat. No. 4,791,931 to John B. Slate of Los Angeles, Calif., a device is disclosed for use in a pulse generator for cardiac pacemaking. The system utilizes a pressure transducer implanted with the pacemaker located on the proximal axillary artery. In Slate, a method is disclosed for the regular pacing of the heart in response to changes in blood pressure utilizing the baroreceptor naturally found in the body. The baroreceptor reflex response changes according to physiological need. Again in Slate, nothing is disclosed in the way of cardioverting or defibrillation, or pacemaking combined with cardioverting or defibrillating. The prior art methods of sensing the baroreceptor nerves in the body have failed to provide a method of cardioverting or defibrillation. Therefore, this invention has the objective of providing a baroreceptor nerve based cardioverter/cardiac pacemaker that is responsive to physiological need.

SUMMARY OF THE INVENTION

It is one object of the invention to provide a cardioverter/pacer having a cardioverting signal to a heart having a timing controlled by the regulation signals detected in the baroreceptors of the body.

It is another object of the invention to provide a cardioverter/pacer having a pacing output based on the variable rhythm controlled by regulation signals detected in the baroreceptors of the body.

It is yet another object of the invention to provide a cardioverter/pacer having a neurosensing electrode around the carotid sinus nerve to provide an amplifier with an automatic gain control and band pass filter.

It is another object of the invention to provide a cardioverter/pacer having a frequency-to-voltage converter with a signal from an automatic gain control amplifier.

It is yet another object of the invention to provide a cardioverter/pacer having an analog-to-digital converter with a voltage converted as an input to a microprocessor.

It is yet another object of the invention to provide a cardioverter/pacer wherein a microprocessor drives a telemetry coil, either/or pacing output and defibrillation lead.

The invention utilizes the baroreceptor nerves found in the body. A neurosense electrode is placed around the carotid sinus nerve and a sense amplifier with automatic gain control and an integral band pass filter provides a frequency-to-voltage converter with a frequency proportional to the stimulus received from the carotid sinus nerve. The voltage from the frequency-to-voltage converter is sent to the analog-to-digital converter where it is bussed to a microprocessor. The microprocessor then drives a pacing lead and in the presence of a cardiac signal the microprocessor provides a cardioverting signal to the cardioverting lead if ventricular arrhythmia is sensed. The microprocessor also drives a telemetry coil and receives ventricular information from the ventricular sensing lead.

Other objects, features and advantages of the present invention will become apparent to those skilled in the art through the Description of the Preferred Embodiment, Claims, and drawings herein wherein like numerals refer to like elements.

BRIEF DESCRIPTION OF THE DRAWINGS

To illustrate the invention, a preferred embodiment of this invention will be described hereinafter with reference to the accompanying drawings. The preferred embodiment concerns a cardioverting pacemaker featuring a baroreceptor input to provide natural rhythms and an appropriate ventricular signal upon cardioverting, to the heart.

FIG. 1 shows generally a schematic of one embodiment of the cardioverting/pacemaking invention.

DESCRIPTION OF THE PREFERRED EMBODIMENT

Figure 2A:
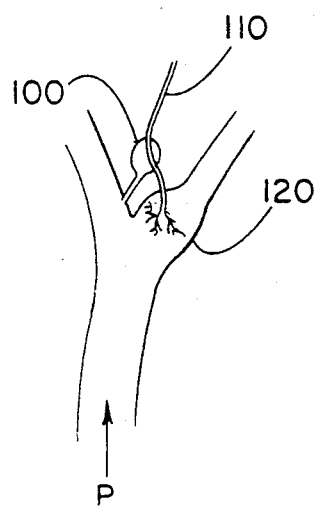
FIGS. 2A, 2B and 2C show schematically carotid sinus stretch receptors and blood pressure relationships therein.

FIG. 1 shows a schematic block diagram of the circuitry required to sense the carotid sinus nerve activity including means for amplifying 16, means for converting frequency to voltage 20, means for converting analog signals to digital signals 24, telemetry means 32, microprocessor means 28, means for providing a pacing output 46, means for providing a defibrillation output 48 and means for ventricular sensing 44. The carotid sinus nerve 10, for example, is wrapped by a sensor 12. As discussed below, other nerve bundles may also be employed in accordance with the invention, these include the vagus nerve, sympathetic cardiac nerve and sympathetic vasoconstrictor nerves. However, the invention is described herein mainly in terms of its use with the carotid sinus nerve, although it will be understood that the use of the invention is not so limited. Typically, the neurosensor may advantageously consist of two ring electrodes made of an inert metal. The rings may be advantageously spaced two to three millimeters apart. Both rings are incorporated into a sleeve made of a biocompatible elastic material such as silicon rubber. One such sensing device is disclosed in U.S. Pat. No. 4,590,946 to Gerald E. Lobe of Clarksburg, Md. In Lobe, a surgically implanted electrode which includes two elements imbedded in a helically long substrate made of an integral material is disclosed. The contact elements are made of electrical leading conductors which are encased in a substrate and extend from a common end of the substrate to a contact element. The substrate is then wound around the nerve bundle in a helical fashion to contact the elements against the nerve. A membrane is subsequently wrapped around the substrate to insulate the electrode system. The lead in conductors are anchored to relieve strain on the electrode system. U.S. Pat. No. 4,590,946 is hereby incorporated by reference. The signals carried by the nerve fiber 10 and which are picked up by the neurosensor 12 consist of a train of action potentials of constant amplitude. The frequency of these action potentials varies as a function of arterial blood pressure. Specifically, as arterial pressure increases, the frequency of action potentials increases.

Figure 2B:
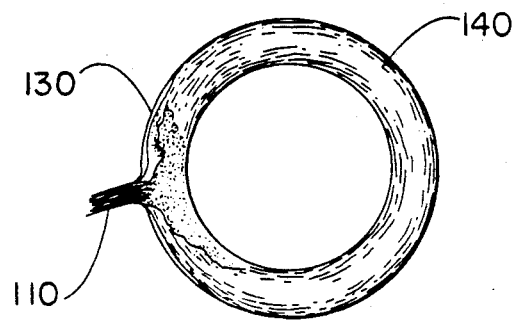

FIG. 2A is a schematic diagram of the carotid sinus region in the human body. This region includes a carotid body 100, carotid sinus nerve 110, and carotid sinus 120. Pressure, denoted by arrow P, is illustrative of blood pressure present in the carotid sinus. FIG. 2B shows a more detailed cross sectional view of the carotid artery 130 where the carotid sinus nerve 110 is stretched over the carotid artery 130 which includes a smooth muscle portion 140.

Figure 2C:
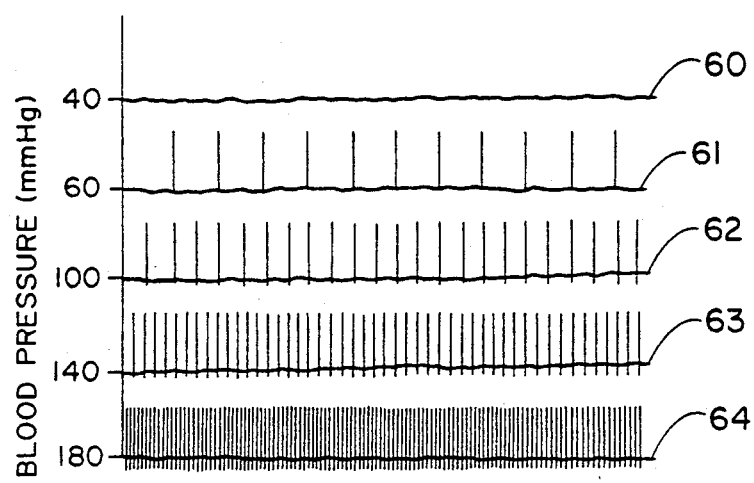

Referring now to FIG. 2C a graph of action potential versus time for various blood pressures is shown. In this diagram, pressure is assumed to be steady. The signals carried by the nerve fiber 10 and which are picked up by neurosensor 12 consist of a train of action potentials 60, 61, 62, 63 and 64. The frequency of these action potentials varies as a function of arterial blood pressure. Specifically, as arterial pressure increases, the frequency of action potentials increases. Note that in graph 60 where the pressure in millimeters of mercury is 40 mm Hg, the carotid sinus signal vanishes. Under normal conditions of varying arterial pressures which occur during the cardiac cycle, the action potential will constantly vary in frequency with maximum frequency occurring at high pressures during systole (contraction of the heart) and minimum frequency occurring at low pressure during diastole (relaxation of the heart).

Figure 3A:
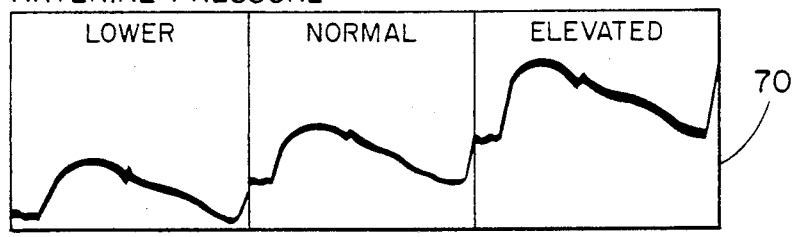
FIGS. 3A-3E are graphic illustrations of the carotid sinus reflexes showing the arterial pressure, carotid sinus nerve impulses, vagus nerve impulses, sympathetic cardiac nerve, and sympathetic vasoconstrictor.
Figure 3B:
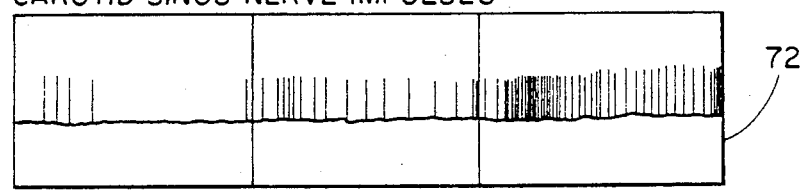
Figure 3C:
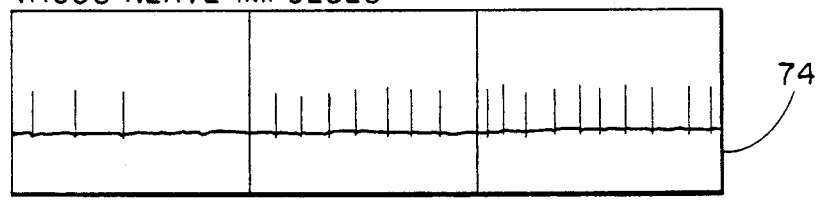
Figure 3D:
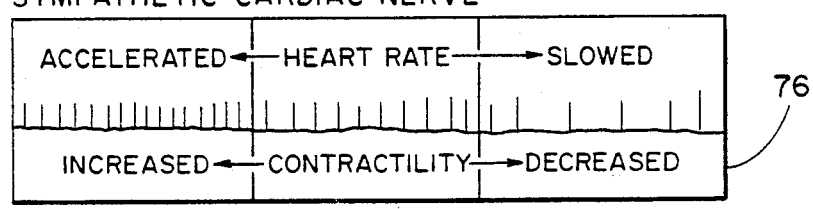
Figure 3E:
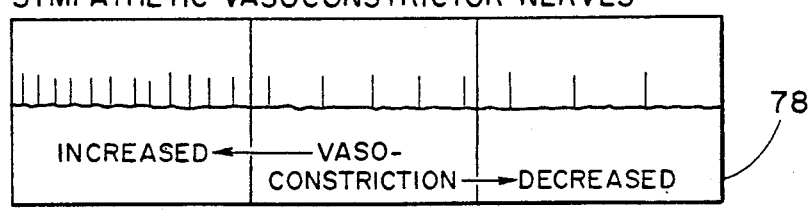

Turning now to FIG. 3A, the carotid sinus reflexes are graphed as a function of low pressure, normal pressure and elevated arterial pressure indicated by graph 70. Graph 72 in FIG. 3B illustrates the response of the carotid sinus nerve impulses. At low pressure the carotid sinus nerve impulses are infrequent. At normal arterial operating pressure the carotid sinus nerve impulses are more regular and at elevated pressures are more frequent. The carotid sinus nerve reflexes are at the highest frequency reaching a peak in the elevated pressure diagram 70. Other nerve responses such as the vagus nerve impulse, sympathetic cardiac nerve impulse and sympathetic vasoconstrictor nerve impulses are also shown in FIGS. 3C, 3D and 3E in graphs 74, 76 and 78, respectively. The relationships shown in FIGS. 3A-3E are well understood by those skilled in the art. Therapies, as discussed below, may be based upon these relationships and implemented in accordance with the present invention.

Referring again to FIG. 1, the sense amplifier 16, which advantageously includes an automatic gain control and band pass filter, receives information from the neurosensor 12. Even though the neurosignal from the carotid sinus nerve is constant, some long term drift in signal amplitude from the nerve will occur. This is due to changes in the nerve tissue and changes in the electrode and nerve fiber interface. The automatic gain control will maintain a constant output level of the amplifier in the presence of long term drift. Amplifier 16 may also include a band pass filter to reject noise which may be present in the nerve signal. The noise may include biologic noise such as action potentials from other nerve fibers as well as electrical signals caused by contraction of muscles in the area of the nerve electrode. The noise may also include external signals such as power line noise or radio frequency coupled into the body. The band pass filter incorporated in amplifier 16 may typically have a low frequency cutoff of 300 hertz to eliminate biologically induced signals and line power noise signals, and a high frequency cutoff of 5000 hertz to eliminate radio frequency noise. Amplifier 16 may be constructed according to well known techniques and electronic design rules.

Connected to the amplifier 16 by conductor 18 is the frequency-to-voltage converter means 20. Circuit 20 provides a voltage output which is proportional to the frequency of the signal applied to the input in accordance with well known principles. Because the frequency of the input is a function of arterial pressure, the output of the frequency-to-voltage converter 20 is in one-to-one correspondence with arterial pressure. In effect, the frequency-to-voltage converter demodulates the frequency modulated pressure signal created by the baroreceptors located in the carotid sinus and transmitted along the carotid sinus nerve. Connected to the frequency-to-voltage converter is the analog-to-digital converter means 24. The analog-to-digital converter 24 converts the analog output signal on line 22 from the frequency-to-voltage converter means 20, which represents arterial pressure, to a digital signal which is further processed by the microprocessor 28. The analog-to-digital converter may be fabricated in accordance with designs well known to those skilled in the art. The microprocessor 28 reads additional signals on bus 26 from the analog-to-digital converter 24 and then processes these signals based on therapies loaded in its operating software. These therapies serve to regulate the stimulus rate of the cardiac pacemaker based on the arterial pressure signals detected from the carotid sinus nerve and processed by the electronics just described. The processor provides the stimulus to the heart by sending appropriate control signals to either the pacing output circuitry 46 or the defibrillation circuitry 48. The telemetry circuits 32 are connected to the microprocessor 28. The telemetry circuit 32 communicates program and diagnostic data between the implanted pacemaker and external programmer through line 30. Information that provides ventricular sense signals is sent through ventricular sensing device 44 to the processor through line 36. In the presence of acceptable pacing signals from the ventricular sensor 44 which represent intrinsic cardiac activity, the processor will not provide stimuli to the heart. Several alternative therapies may be applied to the pressure signals by the processor 28. In one embodiment, the processor may include therapies for detecting signal minimum and signal maximum values which occur during each cardiac cycle. These values can then be used to determine relative diastolic pressures and systolic pressure. The difference can be calculated to obtain pulse pressure.

An alternate therapy may also be included in which true systolic and diastolic pressures, taken with standard measurement methods, are entered into the pacemaker microprocessor by the physician via an external programmer. These values may then be used to convert the relative values described in the first therapy above into an absolute pressure value. An alternate therapy may be present in the processor which may allow for the transmission of the calibrated signals from the carotid sinus sensor to the external programmer. This may allow the programmer to display continuous arterial pressure waveforms obtained for the pacemaker for diagnostic use by the physician. An additional therapy for regulating the pacing rate based on the pressure signals found in the body may advantageously be included to follow the reaction of the body at the onset of exercise. During exercise, vascular resistance decreases due to dilation of blood vessels which occurs to allow greater blood flow to muscle tissue. In normal patients, an increase in heart rate also occurs with exercise, resulting in pressures that are above the pressure prior to exercise. In the absence of this increased heart rate due to the disease of the heart, the blood vessel dilation mentioned previously will tend to cause a decrease in blood pressure. Therefore, one possible therapy for regulating heart rate in response to exercise, may advantageously consist of a method for detecting this blood pressure decrease. The processor may advantageously respond to such a decrease by causing an increase in stimulus rates until the blood pressure returned to a value at or slightly above the value which existed prior to the onset of exercise.

Recovery from exercise occurs in a similar manner. At the end of exercise, blood vessels constrict causing a transient increase in pressure. The processor detects this increase and reduces the heart rate until the pre-exercise pressure value is obtained.

The microprocessor may advantageously include a baseline tracking algorithm to track long term changes in either the patient's blood pressure or in the frequency-to-pressure characteristic of the carotid sinus signal caused by adaptation of the nerve fibers. In this way, the processor responds with a pacing stimulus change only to short term pressure changes caused by exercise onset and completion. Additionally, other circuits may optionally be incorporated to provide more sophisticated rate control algorithms. These might include atrial sense and pacer apparatus for dual chamber pacing, for example. They may also include traditional neurosensors for detecting blood oxygen or carbon dioxide levels in conjunction with the blood pressure sensors for more precise control of pacing rates. An additional application for the cardio sinus nerve sensor is for the detection of tachycardia or fibrillation in an automatic implantable cardioverter defibrillator.

Referring again to FIG. 1, note that the microprocessor may optionally produce a defibrillation output 48 instead of or in addition to a pacing output 38. The therapy for tachycardia fibrillation detection will consist of the following addition to the therapy described previously. During fibrillation or pathologic heart tachycardia, blood pressure falls rapidly due to the loss of blood flow. This rapid drop in blood pressure is detected by the processor and causes it to send appropriate control signals to the defibrillation output circuit 48. Defibrillation output circuit 48 responds by delivering a fibrillation shock to the heart through the defibrillation lead 50. As with the pacemaker application, the defibrillator may incorporate additional signals for more sophisticated detection algorithms. In this case, it might include atrial and ventricular signals for rates of detection. The pacing and defibrillation circuits may, of course, be combined into a single device capable of providing both functions as shown.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A programmable baroreceptor nerve sensing based cardioverter and pacemaker apparatus comprising:
   (a) a neurosense electrode having a neurosignal output wherein the neurosense electrode is in contact with a sensed nerve and provides a neurosignal thereon;
   (b) a neurosense amplifier having an automatic gain control and band pass filter including an input connected to the neurosignal output wherein the neurosense amplifier further has an output and provides an amplified neurosignal thereon;
   (c) a frequency-to-voltage converter having a first input connected to the neurosense amplifier output wherein the frequency-to-voltage converter has an output and provides a voltage converted signal thereon proportional to the frequency of the amplified neurosignal;
   (d) an analog-to-digital converter including an input connected to the frequency-to-voltage converter output wherein the analog-to-digital converter has an output and provides a digital signal representative of the voltage converted signal thereon; and
   (e) a microprocessor for executing a pressure responsive control algorithm in response to the representative digital signal including an input connected to the analog-to-digital converter output wherein the microprocessor has an input/output port, an output for providing pacing signals according to the control algorithms and a second output for providing defibrillation signals according to the control algorithm.

2. The apparatus of claim 1 wherein the neurosense electrode comprises a set of two coils surrounding the sensed nerve.

3. The apparatus of claim 1 wherein the neurosense electrode is comprised of a spiral wound coil.

4. The apparatus of claim 1 wherein the microprocessor receives 8 bits of data from the analog-to-digital converter.

5. The apparatus of claim 1 wherein the sense amplifier with automatic gain control and band pass filter passes analog signals in the frequency range of 300 to 5,000 Hertz.

6. The apparatus of claim 1 wherein the sensed nerve comprises the carotid sinus nerve.

7. The apparatus of claim 1 wherein the sensed nerve comprises the vagus nerve.

8. The apparatus of claim 1 wherein the sensed nerve comprises the sympathetic cardiac nerve.

9. The apparatus of claim 1 wherein the sensed nerve comprises the sympathetic basal constrictor nerves.

10. The apparatus of claim 1 wherein the microprocessor also outputs a cardiac pacing signal.

11. The apparatus of claim 10 wherein the microprocessor also outputs a cardioverting signal.

12. The apparatus of claim 1 further comprising a means for ventricular sensing with a first output connected to the first input of the microprocessor.

13. A programmable baroreceptor nerve sensing based cardioverter and pacemaker apparatus comprising:
   (a) means for sensing neurosignals having a neurosignal output;
   (b) means for amplifying neurosense signals including an automatic gain control and band pass filter having an input connected to the neurosignal output wherein the neurosense amplifier means has an output for providing amplified neurosense signals;
   (c) means for converting frequency to voltage having an input connected to the output of the neurosense amplifier means wherein the frequency-to-voltage converter means has an output and wherein the amplified neurosense signals are converted to converted analog signals having voltage amplitudes proportional to the frequency of the amplified neurosense signals at the converter output;
   (d) means for converting analog signals to digital signals having an input connected to the converter output of the frequency-to-voltage converter means wherein the analog-to-digital converter means has an A/D output for providing digital signals proportional to the converted analog signals; and
   (e) microprocessor means for executing a pressure responsive control algorithm with a first input connected tot he A/D output of the analog-to-digital converter means wherein the microprocessor means includes an input/output port, a first output for providing a cardiac pacing signal according to the control algorithm, and a second output for providing a cardioverting signal according to the control algorithm, wherein the control algorithm executes in response to the digital signals on the A/D output.

14. The apparatus of claim 13 wherein the neurosensing means comprises a set of two coils surrounding a sensed nerve.

15. The apparatus of claim 14 wherein the neurosensing means is comprised of a spiral wound coil.

16. The apparatus of claim 14 wherein the sensed nerve comprises the carotid sinus nerve.

17. The apparatus of claim 14 wherein the sensed nerve comprises the vagus nerve.

18. The apparatus of claim 14 wherein the sensed nerve comprises the sympathetic cardiac nerve.

19. The apparatus of claim 14 wherein the sensed nerve comprises the sympathetic basal constrictor nerves.

20. The apparatus of claim 13 wherein the digital signal comprises 8 bits of data from the analog-to-digital converter.

21. The apparatus of claim 13 wherein the sense amplifier means with automatic gain control and band pass filter passes analog signals in the frequency range from 300–5,000 Hertz.

22. The apparatus of claim 13 further including a telemetry means including an input/output port connected to the microprocessor input/output port.

23. A method for operating a pacemaker apparatus comprising the steps of:
   (a) sensing neurosignals from a baroreceptor nerve;
   (b) processing the sensed neurosignals and producing a cardioverting control signal in response to the sensed neurosignals; and
   (c) operating the pacemaker to produce cardioverting signals in response to the cardioverting control signal.

* * * * *